US007724873B2

(12) United States Patent
Sakaguchi et al.

(10) Patent No.: US 7,724,873 B2
(45) Date of Patent: May 25, 2010

(54) X-RAY DIAGNOSTIC APPARATUS AND X-RAY DIAGNOSTIC SYSTEM

(75) Inventors: Takuya Sakaguchi, Shioya-gun (JP); Toshihiro Rifu, Saitama (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 11/861,903

(22) Filed: Sep. 26, 2007

(65) Prior Publication Data

US 2008/0212740 A1  Sep. 4, 2008

(30) Foreign Application Priority Data

Oct. 2, 2006   (JP)   .............................. 2006-271024

(51) Int. Cl.
*H05G 1/64*   (2006.01)
(52) U.S. Cl. ......................................... 378/98; 378/205
(58) Field of Classification Search .................. 378/98, 378/62, 94, 95, 96, 98.2, 98.3, 98.8, 98.9, 378/98.11, 195–198, 205, 207
See application file for complete search history.

(56) References Cited

U.S. PATENT DOCUMENTS 6,195,450 B1 *  2/2001  Qian et al. ................... 382/130
6,944,269 B2 *  9/2005  Schmitt ........................ 378/115
2002/0041654 A1 *  4/2002  Hayashi ........................ 378/196

OTHER PUBLICATIONS

N. Yamamura, et al., "Computational Biomechanics", Riken Symposium, Mar. 7, 2006, pp. 174-181.

* cited by examiner

*Primary Examiner*—Hoon Song
(74) *Attorney, Agent, or Firm*—Oblon, Spivak, McClelland, Maier & Neustadt, L.L.P.

(57) ABSTRACT

An X-ray diagnostic apparatus includes a bed, an X-ray generating unit, an X-ray detection unit, a support which movably supports the X-ray generating unit and the X-ray detection unit, an X-ray application switch which triggers generation of X-rays from the X-ray generating unit, an operation unit for moving the X-ray generating unit and the X-ray detection unit, an image generating unit which generates an image on the basis of an output from the X-ray detection unit, a display unit which is placed near the bed and displays the image, and a simulation image generating unit which generates a simulation image from stored data during a simulation period in accordance with operation of the X-ray application switch and operation of the operation unit.

14 Claims, 6 Drawing Sheets

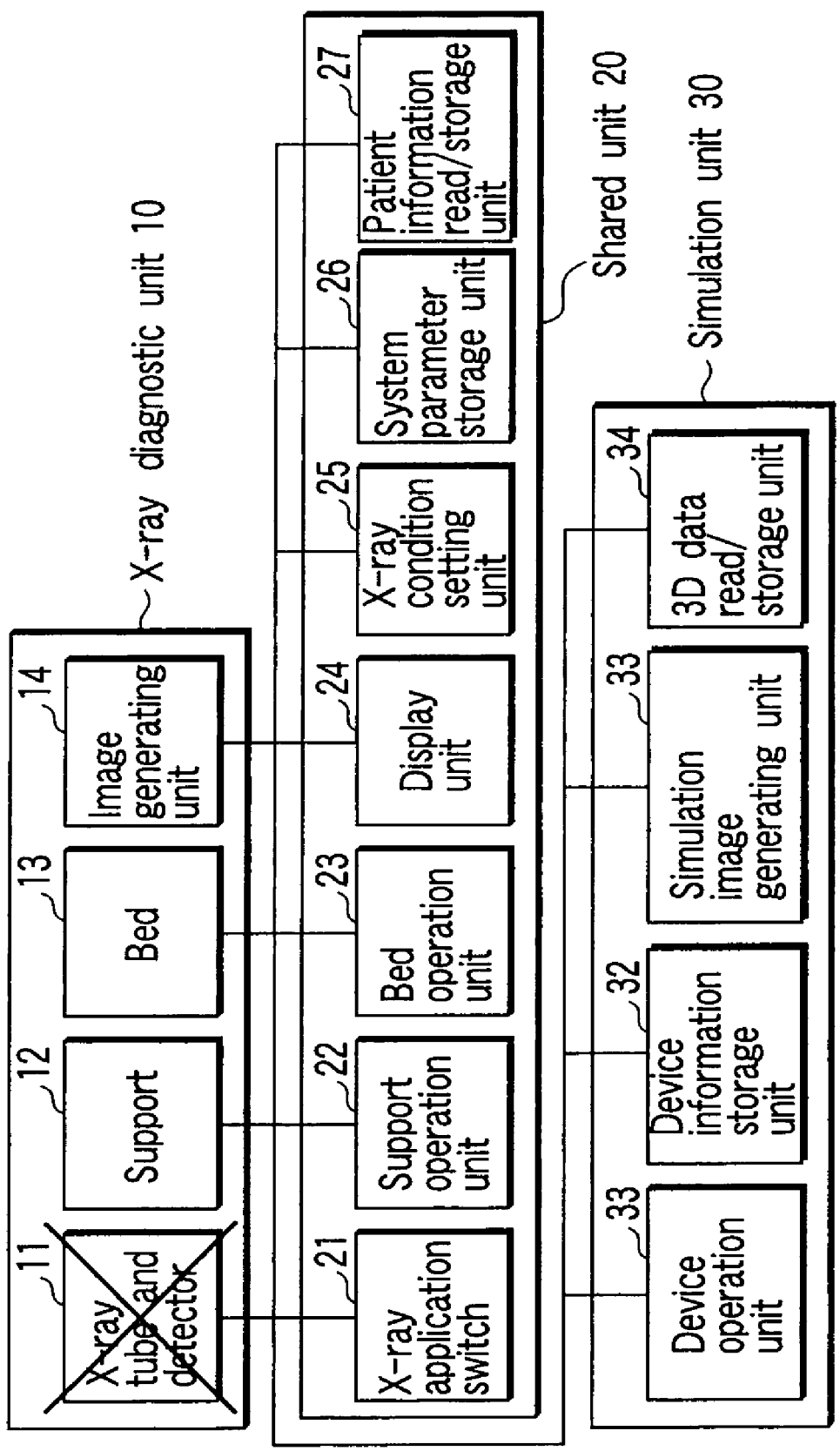
F I G. 3

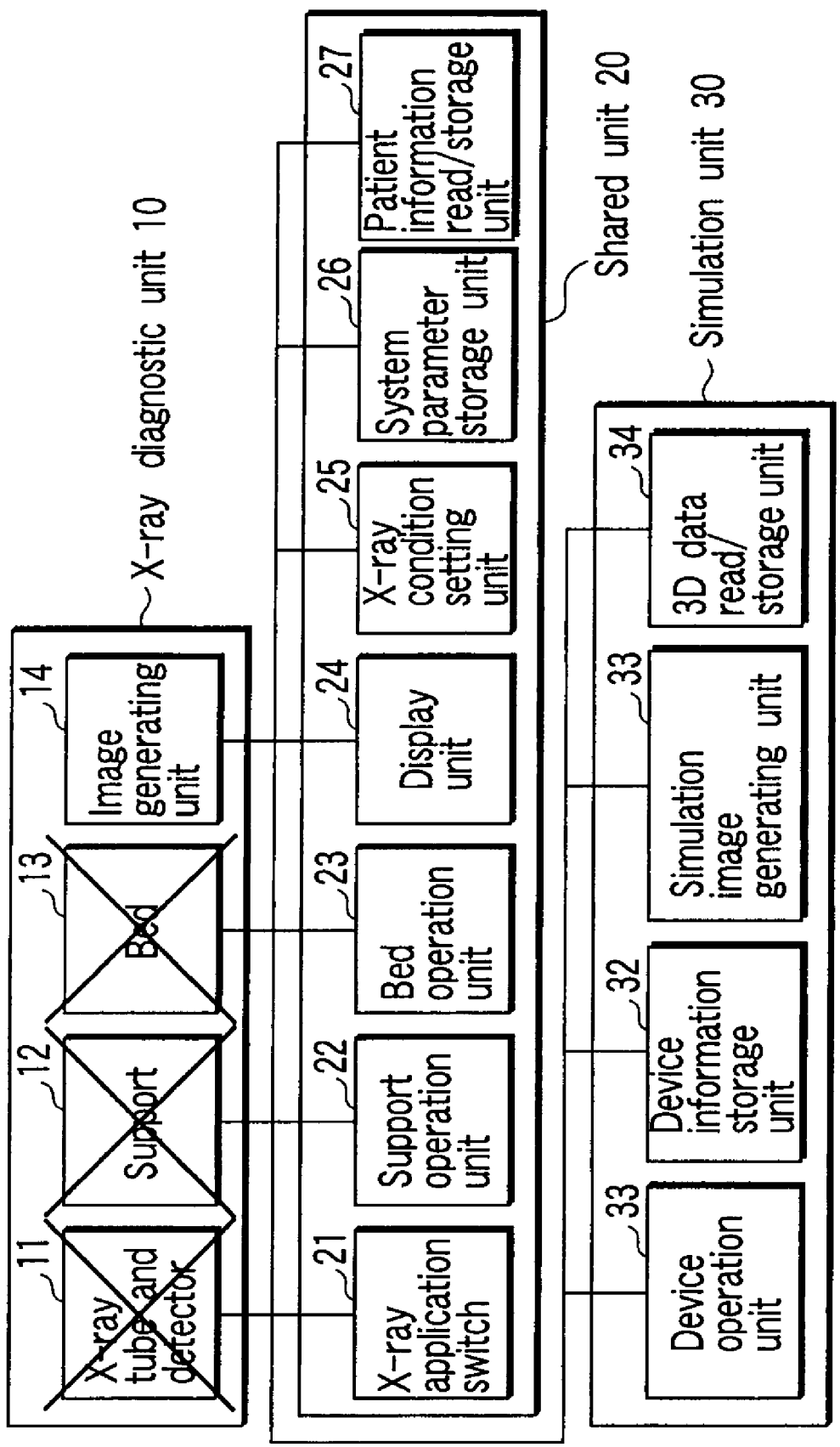
F I G. 4

US 7,724,873 B2

X-RAY DIAGNOSTIC APPARATUS AND X-RAY DIAGNOSTIC SYSTEM

CROSS-REFERENCE TO RELATED APPLICATIONS

This application is based upon and claims the benefit of priority from prior Japanese Patent Application No. 2006-271024, filed Oct. 2, 2006, the entire contents of which are incorporated herein by reference.

BACKGROUND OF THE INVENTION

1. Field of the Invention

The present invention relates to an X-ray diagnostic apparatus and an X-ray diagnostic system.

2. Description of the Related Art

Intravascular treatment using a guide wire or catheter is widely practiced for blood vessels in the brain, carotid artery, lower limb, and the like. This catheterization is low in invasiveness for patients. It is however difficult to learn catheterization.

Recent technical advances in X-ray computed tomography (CT) has increased the chance of applying CT images to vascular diagnosis. This has decreased the opportunity for doctors to improve their skills in angiographic examinations. For this reason, some learned societies worry about an increase in the number of doctor who lack in training.

Simulation systems for guide wire or catheter training have been developed to solve the lack of training. A simulation system reads in the three-dimensional volume data of blood vessels which are generated by CT. The simulation system combines a catheter image corresponding to the distance and the amount of rotation by which an operator has operated the catheter with a projection image derived from three-dimensional volume data, and displays the resultant image. This system also has a function of issuing a warning on a monitor when the guide wire moves outside the blood vessel region of three-dimensional volume data. See, for example, "COMPUTATIONAL BIOMECHANICS", RIKEN SYMPOSIUM, 7 Mar. 2006, RIKAGAKU KENKYUJO (RIKEN), pp. 174-181.

A simulation system is provided by one computer, and hence provides good performance by itself. The state in which a doctor operates the computer apparently differs from the state in which the doctor actually uses a catheter for a patient.

The conventional simulation system therefore is low in training performance.

BRIEF SUMMARY OF THE INVENTION

It is an object of the present invention to allow to execute training for a surgical operation using a catheter or the like in a situation similar to that of actual treatment.

According to an aspect of the present invention, there is provided an X-ray diagnostic apparatus comprising a bed, an X-ray generating unit, an X-ray detection unit, a support which movably supports the X-ray generating unit and the X-ray detection unit, an X-ray application switch which triggers generation of X-rays from the X-ray generating unit, an operation unit for moving the X-ray generating unit and the X-ray detection unit, an image generating unit which generates an image on the basis of an output from the X-ray detection unit, a display unit which is placed near the bed and displays the image, and a simulation image generating unit which generates a simulation image from stored data during a simulation period in accordance with operation of the X-ray application switch and operation of the operation unit.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 3 is a block diagram showing the units which can be operated in a full mode in this embodiment;

FIG. 4 is a block diagram showing the units which can be operated in a silent mode in this embodiment;

DETAILED DESCRIPTION OF THE INVENTION

An embodiment of the present invention will be described with reference to the views of the accompanying drawing. This embodiment is provided as an X-ray diagnostic apparatus or an X-ray diagnostic system. The X-ray diagnostic apparatus of this embodiment includes part (simulation unit) of a simulation apparatus. The simulation apparatus comprises the simulation unit and part of the X-ray diagnostic apparatus. The X-ray diagnostic system of this embodiment comprises an X-ray diagnostic apparatus and a simulation apparatus. Part of the simulation apparatus is shared as part of the X-ray diagnostic apparatus.

Figure 1:
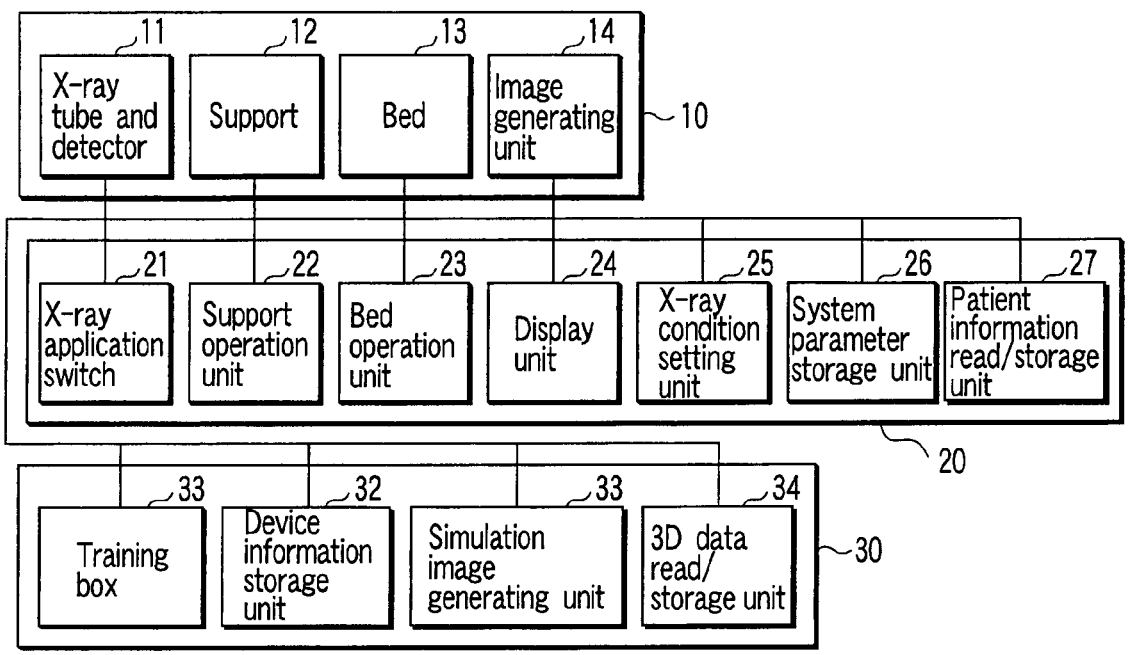
FIG. 1 is a block diagram showing the schematic arrangement of an X-ray diagnostic apparatus according to an embodiment of the present invention.

This embodiment will be described in detail below. FIG. 1 is a block diagram showing the schematic arrangement of an X-ray diagnostic apparatus according to an embodiment of the present invention. The X-ray diagnostic apparatus shown in FIG. 1 comprises an X-ray diagnostic unit 10 for performing X-ray diagnosis, a simulation unit 30 for performing simulation for training, and a shared unit 20 which is shared by the X-ray diagnostic unit 10 and the simulation unit 30.

The X-ray diagnostic unit 10 includes an X-ray tube, detector 11, support 12, bed 13, and image generating unit 14. The X-ray tube generates X-rays. The detector detects X-rays transmitted through a subject to be examined. Note that the detector is, for example, an I.I. (image intensifier) or solid-state detector. The support 12 supports the X-ray tube and the detector. The detector faces the X-ray tube. The bed 13 allows a patient to be placed thereon and can move in the vertical and horizontal directions. The image generating unit 14 generates image data on the basis of an output from the detector.

The shared unit 20 comprises an X-ray application switch 21, support operation unit 22, bed operation unit 23, display unit 24, X-ray condition setting unit 25, system parameter storage unit 26, and patient information read/storage unit 27. The X-ray diagnostic apparatus according to this embodiment allows to select an operation mode between the "simulation mode" and the "X-ray diagnostic mode" by using, for example, a change-over switch or a selection switch. More specifically, in the "simulation mode", a signal from the shared unit 20 is sent to the simulation unit 30. In the "X-ray diagnostic mode", a signal from the shared unit 20 is sent to the X-ray diagnostic unit 10. Each component of the shared unit 20 will be described in detail later.

The simulation unit 30 comprises a training box 31, device information storage unit 32, simulation image generating unit 33, and 3D data read/storage unit 34.

Figure 6:
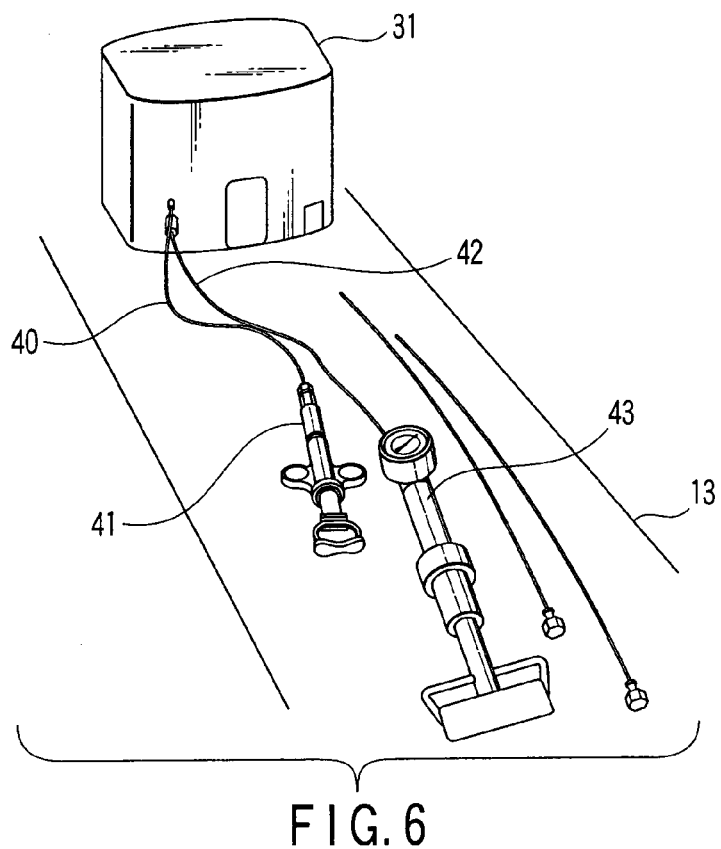
FIG. 6 is a view showing a training box in FIG. 1.

As exemplified by FIG. 6, the training box 31 is a model which allows a doctor to simulate an operation using a device such as a micro catheter or a guide wire. The training box 31 has an insertion opening through which a catheter or a guide wire is inserted. The training box 31 has a function of detecting the advance distance, advance direction, and axial rotation angle of the catheter or the like inserted through the insertion opening. The device information storage unit 32 is a unit which stores the type, length, thickness, hardness, company name, stock, and the like of the catheter to be inserted into the training box 31. The 3D data read/storage unit 34 reads in and stores the 3D data (e.g., CT or MRI data) of a patient which is acquired in advance.

Figure 7:
FIG. 7 is a view showing an example of a simulation image generated by a simulation image generating unit in FIG. 1.

The simulation image generating unit 33 generates a projection image (catheter image) of the catheter or the like on the basis of the projection angle set by the support 12, the SID (tube/detector distance) set by the support 12, the advance distance of the catheter or the like detected by the training box 31, the advance direction of the catheter or the like detected by the training box 31, and the axial rotation angle of the catheter or the like detected by the training box 31. The simulation image generating unit 33 generates a projection image of the subject from the 3D data from the 3D data read/storage unit 34 by projection processing corresponding to the projection angle set by the support 12 and the SID set by the support 12. The simulation image generating unit 33 generates a simulation image by combining the catheter image with the projection image to generate a simulation image. FIG. 7 shows an example of the simulation image.

When a CT image is to be used, it is preferable to display an image comprising only a blood vessel. This makes it possible to display only a blood vessel having a level of contrast which actually allows observation using the X-ray diagnostic unit 10 instead of outputting an image which only the X-ray diagnostic apparatus can output. It is also preferable to freely switch display levels. That is, in a case of complete occlusion, this apparatus allows to select whether to display the occlusion region.

Each component of the shared unit 20 will be described in detail below. Each component of the shared unit 20 is basically shared by the X-ray diagnostic unit 10 and the simulation unit 30. This makes it possible to perform training in the simulation mode under the same environment as that at the time of diagnosis. The X-ray application switch 21 is used both as a switch in the diagnostic mode and a switch in the simulation mode. That is, in the X-ray diagnostic mode, while the X-ray application switch 21 is pressed, X-rays are generated, and X-rays transmitted through the subject are detected.

In this mode, an X-ray image is then generated and displayed in real time. In the simulation mode, while the X-ray application switch 21 is pressed, a catheter image is generated by image processing based on the advance distance or the like of the catheter detected by the training box 31 and the projection angle based on the support 12, and a projection image is generated from the 3D data stored in the storage unit 34 on the basis of the projection angle based on the support 12, and a simulation image is generated by combining the catheter image with the projection image.

The support operation unit 22 is placed near the bed 13 and is provided to move and rotate the C-arm 12. The support operation unit 22 is used in both the diagnostic mode and the simulation mode. The bed operation unit 23 is provided to operate the bed. The bed operation unit 23 is used both in the diagnostic mode and the simulation mode. The display unit 24 is provided to display an image at the time of diagnosis, and is also used to display a simulation image in the simulation mode. The X-ray condition setting unit 25 is provided to set X-ray conditions such as a tube voltage and is also used to set X-ray conditions in the simulation mode.

Figure 2:
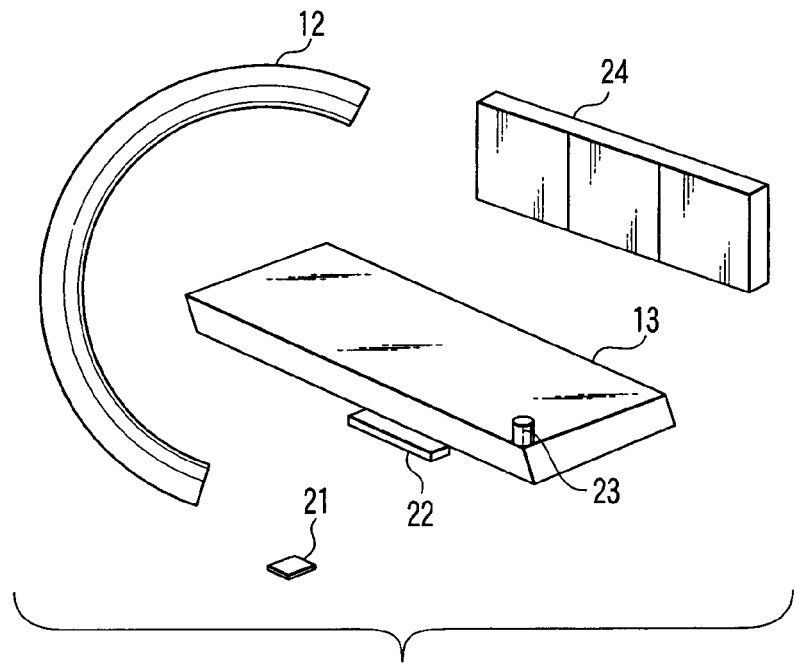
FIG. 2 is a view showing an example of the placement of a support, X-ray application switch, support operation unit, bed, and display unit in FIG. 1.

FIG. 2 is a view showing an example of the placement of the main parts of the X-ray diagnostic apparatus in an X-ray diagnostic room. FIG. 2 shows the X-ray application switch 21, support operation unit 22, bed operation unit 23, and display unit 24 of the shared unit 20. Both in the diagnostic mode and the simulation mode, the support (C-arm) 12 and the bed 13 move/rotate in accordance with the operations of the support operation unit 22 and bed operation unit 23.

In this case, the support 12 (a holder and arm) of the X-ray diagnostic unit 10 rotates/moves in synchronism with the simulation unit 30. When the viewpoint direction is changed with the simulation unit 30, the support 12 rotates through a corresponding angle. When the SID (X-ray source/detector distance: Source Image Distance) is changed with the simulation unit 30, the support 12 moves to change the SID. Note that this synchronous rotating/moving operation can be turned on/off by the simulation mode to be described in detail later. Note that when the viewpoint is changed with the simulation unit 30 to an angle through which the support 12 cannot be mechanically rotated in practice, it is preferable to notify that the support 12 cannot be rotated.

The bed 13 of the X-ray diagnostic unit 10 is configured to move in synchronism with the simulation unit 30. As the simulation unit 30 is moved, the bed 13 moves accordingly. Note that this cooperative moving operation can be turned on/off by the simulation mode.

Figure 8:
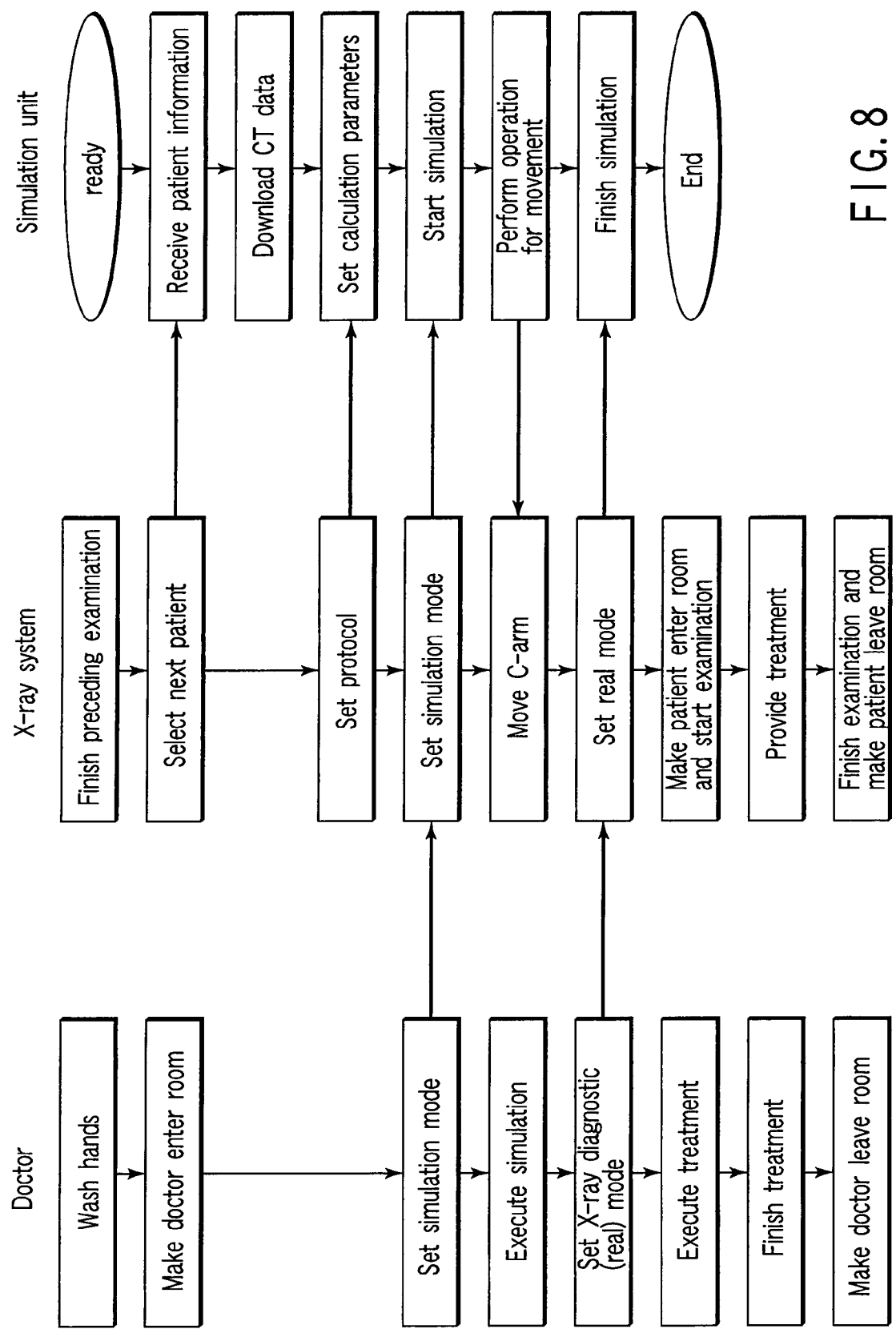
FIG. 8 is a flowchart showing a procedure for switching an X-ray diagnostic mode and a simulation mode in this embodiment.

In addition, a switch for switching between the "X-ray diagnostic mode" and the "simulation mode" is provided for the support operation unit 22 or the X-ray condition setting unit 25 to prevent the operator from erroneously apply X-rays at the time of training simulation. As shown in FIG. 8, operating the mode switch makes it possible to easily switch between the "X-ray diagnostic mode" and the "simulation mode". In the simulation mode, the simulation unit 30 inputs patient information and CT 3D data. The simulation unit 30 inputs a radiography protocol and sets calculation parameters.

In the "simulation mode" as training simulation, the X-ray diagnostic unit 10 is not controlled. More specifically, the X-ray tube generates no X-rays, and the detector does not operate. This "simulation mode" includes a plurality of kinds of modes. This apparatus includes at least three modes as the "simulation mode", namely a "full mode", "safe mode", and "silent mode".

In this case, as shown in FIG. 3, the "full mode" is a mode of performing all operations except for operations associated with the generation and detection of X-rays. In this mode, the X-ray diagnostic unit 10 and simulation unit 30 synchronously operate. The mode is used for general training. In the mode, although the X-ray tube generates no X-rays and the detector 11 does not operate, the support (C-arm) 12 rotates and the bed 13 moves. Note that a pseudo X-ray application sound is produced.

The "safe mode" is a mode which is used when it is not preferable to perform mechanical operation in, for example, a case wherein another staff is controlling the X-ray diagnostic apparatus in the diagnostic room, that is, when it is not preferable to mechanically move (operate) the support 12 and the bed 13. In this case, the respective parameters for the X-ray diagnostic unit 10 are captured, and a sound is produced in synchronism with illumination in the same manner as in the X-ray diagnostic mode. However, only the mechanical movement of the support 12 and bed 13 is inhibited.

The "silent mode" is a mode which is used when it is necessary to perform training in the presence of a patient without letting the patient know it. As shown in FIG. 4, no sound is produced and illumination is not synchronously performed. In addition, the X-ray tube generates no X-rays, and the detector 11 does not operate. Furthermore, no X-ray application sound is produced.

In the "X-ray diagnostic mode", the X-ray application switch 21 outputs an X-ray application signal. In the "simulation mode", the X-ray application switch 21 outputs a signal for displaying a simulation image. In this case, the apparatus preferably includes a pseudo X-ray application switch dedicated to the simulation unit 30. In the simulation mode, the actual X-ray application switch is invalidated, and hence no X-rays are generated. In general, therefore, in the X-ray diagnostic room, when X-rays are applied, a lamp indicating that "X-rays are being applied" which is provided at the entrance door of the room. In the simulation mode, however, the lamp is not turned on.

Note that in some facilities, when X-rays are applied, the illumination in the X-ray diagnostic room is dimmed. It is preferable that the illumination can also be dimmed in the simulation mode.

When the operator operates the support operation unit 22, the support 12 moves regardless of whether the "X-ray diagnostic mode" or the "simulation mode" is set. In addition, when the bed operation unit 23 is operated, the bed 13 moves regardless of whether the "X-ray diagnostic mode" or the "simulation mode" is set. Note that in the silent mode of the "simulation mode", the support 12 and the bed 13 do not move regardless of the operations of the support operation unit 22 and bed operation unit 23.

The display unit 24 includes a fluoroscopic monitor, and displays a simulator image on the fluoroscopic monitor. Assume that a method of displaying additional information is similar to the display method used in the X-ray diagnostic unit provided in the X-ray diagnostic room. For example, in the X-ray diagnostic room having the X-ray diagnostic unit which displays conditions on the left side of the screen, even when simulation is performed, conditions are displayed on the left side of the screen, and the same icons are used.

Figure 5:
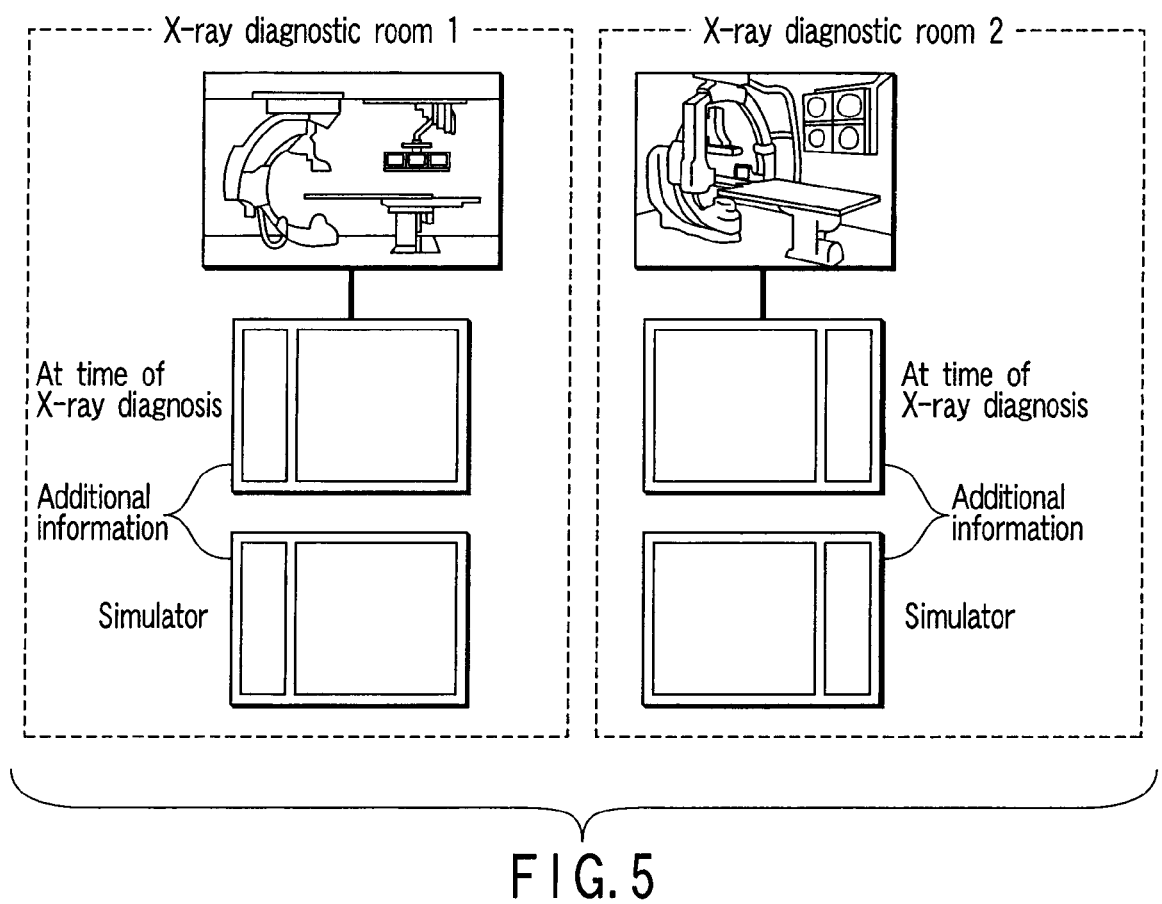
FIG. 5 is a view showing a display example when two X-ray diagnostic rooms are arranged side by side in this embodiment.

As described above, window display is preferably performed in the same manner as on the X-ray diagnostic unit provided in the X-ray diagnostic room. Consider, for example, a hospital in which two X-ray diagnostic rooms are arranged side by side, and identical simulators are introduced, as shown in FIG. 5. In this case, for example, in X-ray diagnostic room 1, when an additional information indication (on which current X-ray conditions and the like are displayed) of the X-ray system is displayed on the left side, the additional information indication of the simulation unit 30 is also displayed on the left side. In X-ray diagnostic room 2, when the additional information indication of the X-ray system is displayed on the right side, the additional information indication of the simulation unit 30 is also displayed on the right side.

The X-ray condition setting unit 25 sets X-ray conditions. The X-ray conditions to be set include a tube voltage (kV), tube current (mA), pulse exposure time (msec), pulse rate, compensation filter, and collimator.

The mode switch is a switch dedicated to switching between the X-ray diagnostic mode and the simulation mode. Assume that, for example, this switch has a geometrical shape that allows detachable connection to a rail of the bed 13.

The system parameter storage unit 26 stores at least one of the following parameters: a system configuration, a protocol, the rotational movable range of the support 12, the moving speed of the support 12, an image processing method (image quality), detector size, field of view (FOV) size, pixel size, an SID range, tube voltage, tube current, pulse exposure time, pulse rate, a compensation filter, a collimator, the movable range of the bed 13, and the like.

In this case, the simulation unit 30 reads in necessary information from the system parameter storage unit 26 and changes an internal parameter on the basis of the read information. The simulation unit 30 then presents the operator with selectable parameters and selectable candidates (limits and ranges) on the basis of the read information. Note that the system parameter storage unit 26 stores different system parameters for each X-ray diagnostic room (i.e., each X-ray diagnostic apparatus). For example, the system parameter storage unit 26 stores parameters corresponding to the X-ray diagnostic unit to be used so as to display a round or rectangular window at the time of simulation depending on whether the detector is an I.I. (image intensifier) or an FPD (Flat Panel Detector).

The patient information read/storage unit 27 reads examination reservation information which has already been read in the X-ray diagnostic apparatus, refers to the patient ID in the examination reservation information, reads in corresponding volume data from the server, and stores it. This makes it possible to perform training while referring to the patient information by using the simulation unit 30.

If the X-ray diagnostic unit 10 is a system having two diagnostic systems (biplane system), the simulation unit 30 preferably displays images in two directions.

It is further preferable that this apparatus includes a registration means (not shown) and positions a past image read in by the simulation unit 30 with the current image diagnosed by the X-ray diagnostic unit 10.

The operation of the X-ray diagnostic apparatus according to this embodiment having the above arrangement will be outlined.

When the operator turns on the X-ray diagnostic unit 10 and the simulation unit 30, the X-ray diagnostic apparatus starts. In this case, the shared unit 20 may operate on either of the power supplies of the X-ray diagnostic unit 10 and the simulation unit 30. The X-ray diagnostic unit 10 and the simulation unit 30 may share a power supply, but preferably uses different power supplies.

When the X-ray diagnostic apparatus starts, the X-ray diagnostic unit 10 reads in patient information by using a hospital information system (not shown). Upon detecting that the patient information is read in the X-ray diagnostic unit 10, the simulation unit 30 copies the patient information to the 3D data read/storage unit 34. On the basis of the patient ID of the patient scheduled to be treated first, the simulation unit 30 searches the image database for a latest CT image of the patient, and downloads volume data from the hospital information system. When treatment plan information is written in the patient information, the simulation image generating unit 33 obtains information such as the size of a catheter to be used, the stent to be used, and the like on the basis of the treatment plan information, and automatically sets internal parameters by referring to the device information storage unit 32. In addition, the simulation image generating unit 33 refers to the system parameter storage unit 26 on the basis of the number of the X-ray diagnostic room, and sets parameter information for the X-ray diagnostic unit 10.

The doctor sets the operation mode to the "simulation mode" with the mode switch in the X-ray diagnostic room upon checking the treatment plan. The doctor then performs training without applying X-rays. In training, the doctor performs simulation in, for example, the "full mode" using the X-ray application switch, X-ray system operation (movement of the arm or selection of a field of view), X-ray image display window, and the X-ray bed 13 of the X-ray diagnostic unit 10. In this case, field of view size, pixel size, SID, tube voltage, tube current, pulse exposure time, pulse rate, image processing parameters, the mechanical rotation limit range of the support 12, and the like of the X-ray diagnostic unit 10 in the X-ray diagnostic room are reflected in the simulation unit 30. In this simulation mode, when the doctor presses the switch, an image is displayed. The support 12 rotates, and the bed 13 moves. An X-ray application sound is produced, and the illumination is synchronously dimmed. In this mode, the warning lamp indicating that X-rays are being applied is off.

When finishing training in the above manner, the doctor switches the mode to the "X-ray diagnostic mode" and provides treatment for the patient when preparation for the patient is complete and the patient enters the room. When the doctor starts treatment, the 3D data read/storage unit 34 of the simulation unit 30 automatically reads in information about a patient scheduled to be diagnosed next, downloads corresponding images, and completes preparation for simulation on the next patient, thereby allowing the doctor to perform training.

As described above, according to the present invention, the X-ray diagnostic apparatus includes the shared unit 20 for the X-ray diagnostic unit 10 and the simulation unit 30 to allow to perform simulation in almost the same environment as that for actual treatment. This makes it possible to implement catheter training or the like in an environment similar to that for actual treatment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus, comprising:
    a bed including a movable table on which a subject to be examined is placed;
    an X-ray generating unit;
    an X-ray detection unit;
    a support which movably supports the X-ray generating unit and the X-ray detection unit;
    an X-ray application switch which triggers generation of X-rays from the X-ray generating unit;
    an operation unit for moving the X-ray generating unit and the X-ray detection unit;
    an image generating unit which generates an image on the basis of an output from the X-ray detection unit;
    a display unit which is placed near the bed and displays the image;
    a detection unit which detects an advance distance, an advance direction, and an axial rotation angle of a catheter or a guide wire during a simulation period; and
    a simulation image generating unit which generates a simulation image from stored data during the simulation period in response to operation of the X-ray application switch and operation of the operation unit, wherein the simulation image generating unit generates the simulation image from the stored data in accordance with the detected advance distance, the detected advance direction, and the detected axial rotation angle.

2. An X-ray diagnostic apparatus according to claim 1, wherein the simulation image generating unit generates the simulation image during a period in which the X-ray application switch is pressed.

3. An X-ray diagnostic apparatus according to claim 1, further comprising:
    an X-ray condition setting unit which sets X-ray conditions for the X-ray generating unit, wherein
    the simulation image generating unit generates the simulation image in synchronism with operation of the X-ray application switch and operation of the operation unit in accordance with the set X-ray condition.

4. An X-ray diagnostic apparatus according to claim 3, wherein the X-ray condition includes at least one of a tube voltage, a tube current, an application time, a pulse rate, a compensation filter, and a collimator.

5. An X-ray diagnostic apparatus according to claim 3, wherein the simulation image generating unit generates the simulation image with brightness and contrast corresponding to the set X-ray condition.

6. An X-ray diagnostic apparatus according to claim 1, wherein the simulation image generating unit generates the simulation image in accordance with a position of the table.

7. An X-ray diagnostic apparatus according to claim 1, further comprising:
    a training box which includes an insertion opening through which a catheter or a guide wire is inserted.

8. An X-ray diagnostic apparatus according to claim 1, wherein the simulation image is displayed on the display unit.

9. An X-ray diagnostic apparatus according to claim 1, further comprising:
    an operation unit which switches between two modes including an X-ray diagnostic mode for performing X-ray diagnosis and a simulation mode for performing simulation.

10. An X-ray diagnostic apparatus according to claim 9, wherein the operation unit is detachable from the bed.

11. An X-ray diagnostic apparatus according to claim 9, wherein the simulation mode includes a full mode of allowing to perform all operations except for X-ray application, a safe mode of inhibiting movement of the support and the bed from the full mode, and a silent mode of inhibiting generation of a warning sound and synchronous operation of an illumination from the safe mode.

12. An X-ray diagnostic system, comprising:
    an X-ray diagnostic apparatus including a bed including a movable top on which a subject to be examined is placed, an X-ray generating unit, an X-ray detection unit, a support which movably supports the X-ray generating unit and the X-ray detection unit, an image generating unit which generates an image on the basis of an output from the X-ray detection unit, and a display unit which is placed near the bed and displays the image;

a detection unit which detects an advance distance, an advance direction, and an axial rotation angle of a catheter or a guide wire during a simulation period; and a simulation apparatus which generates information for simulation on a surgical operation using the X-ray diagnostic apparatus, wherein the simulation apparatus generates a simulation image from stored data in accordance with the detected advance distance, the detected advance direction, and the detected axial rotation angle, wherein part of the simulation apparatus is also used as part of the X-ray diagnostic apparatus.

13. An X-ray diagnostic system, comprising:

an X-ray diagnostic apparatus including a bed including a movable table on which a subject to be examined is placed, an X-ray generating unit, an X-ray detection unit, a support which movably supports the X-ray generating unit and the X-ray detection unit, an image generating unit which generates an image on the basis of an output from the X-ray detection unit, and a display unit which is placed near the bed and displays the image;

a detection unit which detects an advance distance, an advance direction, and an axial rotation angle of a catheter or a guide wire during a simulation period; and a simulation apparatus which generates information for simulation on a surgical operation using the X-ray diagnostic apparatus, the simulation apparatus including a simulation unit configured to generate a simulation image from stored data in accordance with the detected advance distance, the detected advance direction, and the detected axial rotation angle, wherein the simulation unit and part of the X-ray diagnostic apparatus constitute the simulation apparatus.

14. The X-ray diagnostic apparatus according to claim 1, wherein the simulation image generating unit generates the simulation image in accordance with a projection angle set by the X-ray generating unit and the X-ray detection unit.

* * * * *